(12) United States Patent
Gschweitl

(10) Patent No.: US 6,563,576 B2
(45) Date of Patent: May 13, 2003

(54) DIODE LIGHT SOURCE FOR A LINE SCAN CAMERA

(75) Inventor: Karlheinz Gschweitl, Grosspesendorf (AT)

(73) Assignee: Binder + Co. Aktiengesellschaft, Gleisdorf (AT)

( * ) Notice: Subject to any disclaimer, the term of this patent is extended or adjusted under 35 U.S.C. 154(b) by 0 days.

(21) Appl. No.: 09/993,835

(22) Filed: Nov. 6, 2001

(65) Prior Publication Data

US 2002/0054286 A1 May 9, 2002

(30) Foreign Application Priority Data

Nov. 7, 2000 (AT) .............................. 811/00 U

(51) Int. Cl.$^7$ ................................ G01N 21/00
(52) U.S. Cl. ............... 356/237.1; 356/908; 356/909
(58) Field of Search ................ 356/237.1, 908–910; 359/707

(56) References Cited

U.S. PATENT DOCUMENTS 3,859,538 A    1/1975  Mannonen
5,365,084 A    11/1994 Cochran
5,818,810 A  * 10/1998 Okabe .................. 369/126

FOREIGN PATENT DOCUMENTS

| AT | 001264  | 1/1997  |
| DE | 2426866 | 12/1974 |

* cited by examiner

*Primary Examiner*—James Phan
(74) *Attorney, Agent, or Firm*—Collard & Roe, P.C.

(57) ABSTRACT

A lighting apparatus for use with line scan cameras in plants for detecting and recognizing objects in a flow of materials such as goods to be sorted, in which several separately controllable diodes and an optical device are provided, with the diodes being disposed at least in one row next to one another over the width of the respective section of the plant and the optical device regularizes the light emitted by the diodes in such a way that a secure detection of the objects and its properties such as material composition, color, size or the like is ensured by cameras. The optical device comprises two diffusers and an interposed lens.

3 Claims, 1 Drawing Sheet

DIODE LIGHT SOURCE FOR A LINE SCAN CAMERA

The subject matter of the invention is an apparatus for detecting and recognizing objects of a flow of material at a plant section, the flow of material being moved between light sources and the scanning zone of cameras which scan the properties of the objects in the glow of material, such as material composition, color or size and are used for triggering evaluation devices, with the light sources being arranged as diodes which are disposed in rows and are mutually separately controllable with respect to their luminosity and/or frequency of the light as emitted by the same.

In such apparatuses for detecting and recognizing objects, e.g. in sorting plants, cameras, which are mostly line scan cameras, are used. Objects in a flow of materials are moved past said cameras and are recognized and allocated accordingly by the cameras. This recognition and allocation can relate to different properties of the objects such as composition of material, color, size and the like. The information thus obtained is then used to control subsequent process sequences or to also control a separating apparatus which sorts the objects into different fractions.

Translucency is often used in the case of transparent or translucent goods. The light source transilluminates the material to be analyzed, which allows a more reliable recognition such as the individual fractions of a material to be sorted. Light sources for transillumination are usually fluorescent lamps which extend entirely or partly over the width of the respective plant section such as the chute of a sorting plant. Regular light is thus produced over a limited zone which is detected by a line scan camera, which ensures regular lighting conditions within the zone as detected by the camera.

The disadvantage in using a fluorescent lamp is that a decreasing luminous intensity can be detected at the two ends of a fluorescent lamp, so that only a limited area of the fluorescent lamp can be used. As a result it is necessary to construct lighting apparatuses of this kind with a larger width than the recognition zone of the line scan cameras. If several fluorescent lamps are used with several line scan cameras this will lead to an overall width of the plant section which is substantially larger than the recognition zone of the cameras. Even if, for example, a long fluorescent lamp is used for the zones of several line scan cameras as light source, there are still zones at the two ends of the fluorescent lamp which cannot be used by the cameras any longer for secure detection. The lighting apparatus must therefore be substantially wider than the respective plant section. A further disadvantage is that the luminosity of the light source can only be controlled or changed as a whole, so that it is not possible to take influence on any differences in individual cameras distributed over the plant section.

AT 001 264 U1 proposes a measuring system for the contactless scanning of the surface of glass panes with the help of infrared LEDs ("Light Emitting Diodes"). IR photodiodes or phototransistors are used as receiver elements. Due to the preferred usage of light in the infrared spectral range there are no optical devices between the infrared LEDs and the flow of material or the flow of material and the receiver elements.

Infrared light is also used in U.S. Pat. No. 3,859,538, so that no optical devices for the homogenization of the lighting are provided. Moreover, this document relates to an electronic circuit for amplifying the signal of photoelectronic components.

U.S. Pat. No. 5,365,084 discloses a lighting system for high-speed video inspections. LEDs with different wavelengths of the emitted light are used which are disposed in rows. Although this document proposes improvements in signal processing, it does not contain any references to the improvement of the lighting by means of optical measures.

DE 24 26 866 B2 also shows LEDs which are disposed in rows. However, it relates in all other respects to electronic data evaluation. In this case too there are minima in intensity in the planes of symmetry between two LEDs each which may cause problems in the precise identification of elements of the flow of materials.

It is the object of the present invention to eliminate such disadvantages and to develop a compact recognition unit with versatile setting and control features which ensures a regular lighting of the respective plant section. In an apparatus of the first-described type, this is achieved in accordance with the invention by providing an optical device which is disposed between the flow of material and the diodes and comprises a diffuser on the object side, a diffuser on the diode side as well as an interposed lens.

Several diodes are disposed in form of one or several rows adjacent to one another over the entire width of the plant section for recognizing objects such as the chute of a sorting plant or parts thereof. These diodes can be controlled separately from one another, so that the luminosity or also the frequency of the emitted light can be varied in sections along the diodes which are disposed in lines. As required, several diodes can also be subject to a joint control.

Since the diodes represent nearly punctiform light sources, it is decisive for an even lighting of the respective plant section to provide the use of an optical device which allows the light emitted by the diodes to appear in a diffuse way. This allows an even lighting of the zones as detected by the line scan cameras. The optical device according to the invention ensures this regularization of the light as emitted by the diodes and thus ensures a secure detection of the material to be sorted and its recognition by cameras.

It is principally possible in installations for recognizing and detecting objects of a flow of material such as goods to be sorted to irradiate the flow of material either with light and thus to ensure the luminosity required for detection by cameras, or to transilluminate the same with light, which is particularly advantageous in translucent or transparent objects.

Preferably, the camera is a line scan camera, with at least one camera, preferably several cameras, being disposed over the width of the plant section, and the diodes are white-light diodes.

The invention will now be explained in closer detail by reference to the enclosed drawings, wherein.

Figure 1:
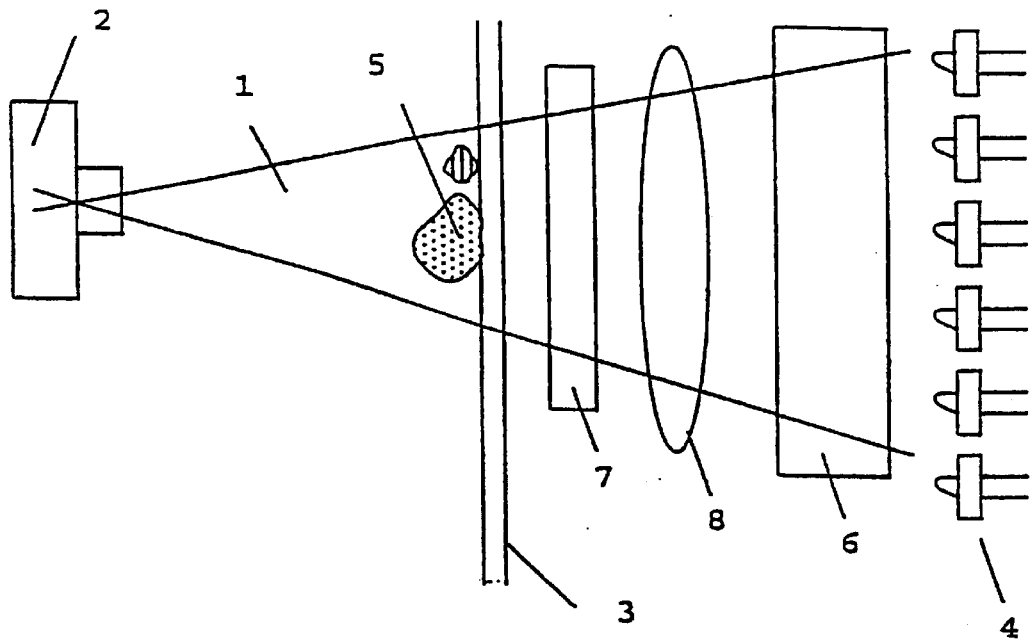
FIG. 1 shows the relative arrangement of cameras, diodes, flow of material and optical device consisting of the two diffusers and a lens.
Figure 2:
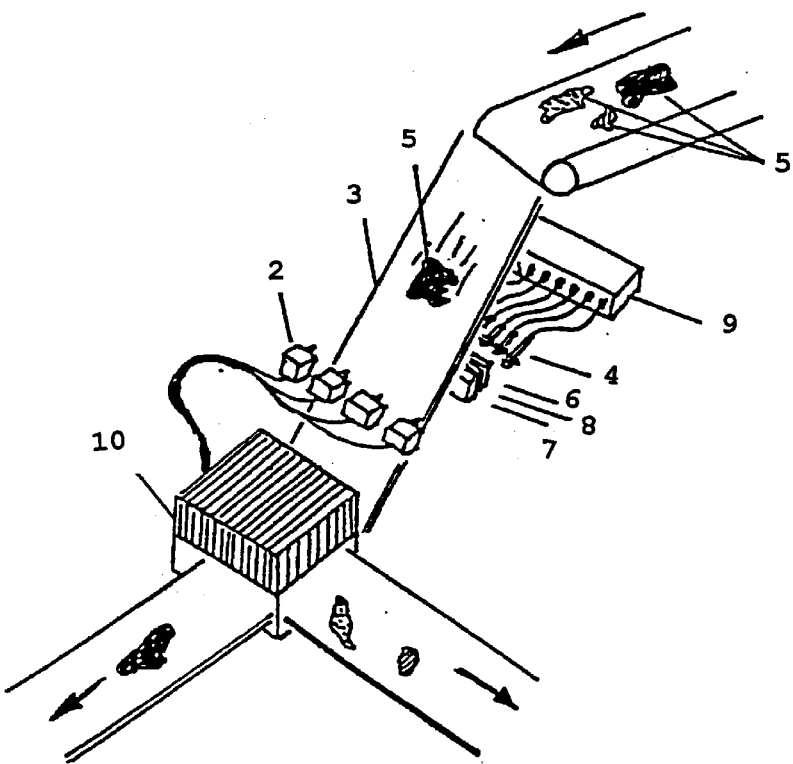
FIG. 2 shows a general diagram to illustrate the application of the invention such as in connection with a downstream sorting device.

FIG. 1 schematically shows the lighting apparatus in accordance with the invention for the detection zone 1 of a line scan camera 2. Line scan cameras are disposed adjacent to one another along the entire width of a plant section 3, e.g. the chute of a sorting plant, for the purpose detecting objects of a flow of material, so that the detection zones 1 of adjacent cameras 2 overlap in the plane of the plant section 3. The section 3 of the plant is made of translucent or transparent material.

Diodes 4, which are preferably white-light diodes, are disposed in form of one or several rows over the entire width of the plant section 3 or parts thereof. Such diodes 4 are used in the illustrated embodiment as light sources for transilluminating transparent or translucent objects 5 and are arranged in such a way that, when seen from the position of the line scan cameras, they are disposed behind the plant section 3. The diodes 4 can be controlled individually by a control device 9. It is thus possible to control the quantity of emitted light for each diode individually along the width of the plant section in order to thus being able to adjust in sections the luminosity as required.

An optical unit which consists of a diffuser 6 on the diode side, a diffuser 7 on the object side and an interposed lens 8 converts the light emitted by the approximately punctiform diode light sources into diffuse light. Lens 8 is used to control and also regularize the light emitted by the diode-side diffuser in its luminous intensity. Material and dimensioning of the diffusers and lens are chosen in such a way that most regular lighting possible of the detection zone 1 is ensured and depends on the respective application, e.g. from the optical density of the objects 5 and the plant section 3, distance between camera 2 and the plant section 3 as well as between plant section 3 and diodes 4 and many more.

During operation the translucent or transparent objects 5 of a flow of material, e.g. goods to be sorted, pass through the plant and reach the section 3 of the plant which is scanned by the line scan cameras 2. An object 5 is transilluminated by diffuse light which is emitted by the lighting apparatus in accordance with the invention. The modifications of the light as emitted by the diodes 4 which are caused by the passage of the object 5 are detected by the line scan cameras 2, thus allowing information to be obtained on various properties of the object 5 such as material composition, color, size or the like. A signal controlled by the recognition process of this camera 2 finally regulates a downstream process step or a downstream separating device 10.

Since in plants with line cameras 2 there are mostly several such cameras which are disposed over the width of the sorting plant section 3 and which each monitor a section of the width and trigger downstream separating devices 10, it is easily possible with the lighting arrangement in accordance with the invention to adjust them in sections to the requirements of the line camera 2. This is not possible in a fluorescent lamp which extends over the entire width of the plant section. The invention thus represents a compact recognition unit with versatile possibilities for adjustment and control.

What is claimed is:

1. An apparatus for detecting and recognizing objects of a flow of material at a plant section, the flow of material being moved between light sources and the scanning zone of cameras which scan the properties of the objects in the flow of material such as material composition color or size and are used for triggering evaluation devices, with the light sources being arranged as diodes which are disposed in rows and are mutually separately controllable with respect to their luminosity and/or frequency of the light as emitted by the same, further comprising an optical device which is disposed between the flow of material and the diodes and comprises a diffuser on the object side, a diffuser on the diode side as well as an interposed lens.

2. An apparatus as claimed in claim 1, wherein the camera is a line scan camera, with at least one camera, preferably several cameras, being disposed over the width of the plant section.

3. An apparatus as claimed in claim 1, wherein the diodes are white-light diodes.

* * * * *